(12) United States Patent
Green et al.

(10) Patent No.: US 9,299,476 B2
(45) Date of Patent: Mar. 29, 2016

(54) POLYMERIC MATERIAL

(75) Inventors: Rylie Adelle Green, Marrickville (AU); Laura Anne Poole-Warren, Coogee (AU); Sungchul Baek, Centennial Park (AU); Penny Jo Martens, Randwick (AU)

(73) Assignee: NEWSOUTH INNOVATIONS PTY LIMITED, Sydney (AU)

( * ) Notice: Subject to any disclaimer, the term of this patent is extended or adjusted under 35 U.S.C. 154(b) by 126 days.

(21) Appl. No.: 13/156,872

(22) Filed: Jun. 9, 2011

(65) Prior Publication Data
US 2012/0100217 A1 Apr. 26, 2012

(30) Foreign Application Priority Data
Oct. 22, 2010 (AU) ................. 2010904729

(51) Int. Cl.
| | |
|---|---|
| A61K 9/00 | (2006.01) |
| A61K 31/795 | (2006.01) |
| A61K 31/727 | (2006.01) |
| A61K 31/713 | (2006.01) |
| A61K 38/18 | (2006.01) |
| A61K 47/30 | (2006.01) |
| A61K 47/32 | (2006.01) |
| A61K 47/42 | (2006.01) |
| A61K 47/36 | (2006.01) |
| A61P 25/00 | (2006.01) |
| A61P 29/00 | (2006.01) |
| B32B 27/06 | (2006.01) |
| B05D 3/10 | (2006.01) |
| H01B 1/12 | (2006.01) |
| C08L 71/02 | (2006.01) |
| A61K 38/39 | (2006.01) |

(52) U.S. Cl.
CPC ............... *H01B 1/122* (2013.01); *C08L 71/02* (2013.01); *A61K 38/39* (2013.01); *Y10T 428/31504* (2015.04); *Y10T 428/31663* (2015.04); *Y10T 428/31725* (2015.04); *Y10T 428/31855* (2015.04)

(58) Field of Classification Search
USPC ................. 424/423; 435/4; 514/779; 604/20; 623/2.42
See application file for complete search history.

(56) References Cited

U.S. PATENT DOCUMENTS

| | | | |
|---|---|---|---|
| 6,365,415 B1 * | 4/2002 | Li et al. .................... | 436/174 |
| 2006/0184092 A1 * | 8/2006 | Atanasoska et al. ........... | 604/20 |
| 2010/0016703 A1 | 1/2010 | Batkin et al. | |

FOREIGN PATENT DOCUMENTS

| | | | | |
|---|---|---|---|---|
| EP | 0149693 | * | 1/1984 | ............. A61L 27/00 |
| WO | 2007/028003 A2 | | 3/2007 | |

OTHER PUBLICATIONS

Ghosh et al., "Electrochemical Characterization of Poly(3,4-ethylene dioxythiophene) based Conducting Hydrogel Networks". Journal of the Electrochemical Society 2000:147(5);1872-1877.*

Poole-Warren, et al., "Engineering cell responses to synthetic polymers via incorporation of active biological molecules", Abstract published during conference held in Dublin on Jun. 11-12, 2010.

Green, et al., "Conducting polymer-hydrogels for medical electrode applications", Sci. Technol. Adv. Mater., 11, pp. 1-13, 2010.

* cited by examiner

*Primary Examiner* — Walter Webb
(74) *Attorney, Agent, or Firm* — Lucas & Mercanti, LLP.

(57) ABSTRACT

Disclosed herein is a polymeric material comprising a conductive polymer substantially homogeneously distributed within a hydrogel. Also disclosed are methods for making the polymeric material and uses for the polymeric material.

15 Claims, No Drawings

POLYMERIC MATERIAL

CROSS-REFERENCE TO RELATED APPLICATION

This application claims the benefit of priority from Australian Patent Application No. 2010904729 filed Oct. 22, 2010, the content of which is incorporated herein by reference.

FIELD OF THE INVENTION

The present invention relates to polymeric materials comprising a hydrogel and a conductive polymer.

BACKGROUND TO THE INVENTION

Conductive polymers are potentially useful in many applications. For example, in applications in which a conductive polymer is provided as an interface between a metal electrode and biological tissue, the conductive polymer exhibits improved impedance characteristics and provides a softer mechanical interface when compared to conventional metal electrodes. The usefulness of conductive polymers in such applications is often limited, however, because they have poor long-term mechanical properties (e.g. they are brittle and non-elastic), poor electrochemical stability (their conductivity decreases over time) and are typically difficult to process (e.g. because they are relatively insoluble).

Attempts have been made to combine conductive polymers with other types of polymers in order to form a hybrid polymeric material which has improved mechanical properties (whilst still being conductive). For example, attempts have been made to incorporate conductive polymers into hydrogel networks, in which hydrophilic polymer chains are cross-linked to form an insoluble polymer network.

However, due to the significantly different chemical and physical properties of conductive polymers and the polymer constituents of the hydrogel, such attempts usually result in the formation of a polymeric material in which the conductive polymers and the hydrogel are phase separated.

SUMMARY OF THE INVENTION

The inventors have surprisingly discovered that it is possible to produce hybrid polymeric materials in which a conductive polymer is not phase separated, but is distributed throughout a hydrogel. Thus, in a first aspect, the present invention provides a polymeric material comprising a conductive polymer substantially homogeneously distributed within a hydrogel.

Polymeric materials comprising a conductive polymer substantially homogeneously distributed within a hydrogel have a number of desirable properties. For example, the hydrogel will improve the mechanical properties of the conductive polymer due to its mechanical softness and elasticity. Such improved mechanical properties enable the polymeric material of the present invention to be more widely used than the conductive polymer itself.

Furthermore, hydrogels have low-fouling surfaces and, because of their high water content, have mechanical properties similar to those of biological tissues. Thus, the polymeric material of the present invention is more biocompatible than the conductive polymer itself and hence is more suitable for use in medical devices that are intended to be implanted into a body.

As the conductive polymer is distributed throughout the hydrogel, then the resultant polymeric material will also be capable of conducting electricity.

In some embodiments, the hydrogel comprises a polymer constituent having covalently bound anionic species, the anionic species being dopants for the conductive polymer. As those skilled in the art will appreciate, a conductive polymer requires a dopant in order for the polymer to form efficiently and be capable of passing electronic or ionic charges. The inventors have discovered that providing suitable dopants (i.e. the anionic species) covalently bound to the polymer constituents of the hydrogel can cause the conductive polymer to be formed intimately with the polymer constituents of the hydrogel.

In some embodiments, the covalently bound anionic species are present in the polymer backbone of the polymer constituent of the hydrogel. In some embodiments, the polymer constituent can be modified to include the covalently bound anionic species (e.g. by grafting an anionic side chain onto the polymer constituent).

In some embodiments, the hydrogel comprises two or more polymer constituents in order to take advantage of the properties each of the polymer constituents impart on the resultant hydrogel. The polymer constituents may, for example, be a biopolymer (i.e. a polymer produced by a living organism or a synthetically produced mimic of a biologically sourced molecule which has similar bioactivity when placed in a biological environment) and/or a synthetic polymer (i.e. a synthetically produced polymer which, in the context of the present invention, is not bioactive to any significant degree).

In some embodiments, the polymeric material further comprises a biologically active substance (e.g. neurotrophins, anti-inflammatory drugs, antibiotics, siRNA or combinations thereof) distributed within the hydrogel. Such biologically active substances can diffuse from the hydrogel over time, for example after insertion into a patient's body.

In a second aspect, the present invention provides a method for producing a polymeric material in which a conductive polymer is substantially homogeneously distributed within a hydrogel. The method comprises:

mixing polymer subunits capable of forming a hydrogel polymer constituent with polymer subunits capable of forming the conductive polymer; and then exposing the mixture to conditions whereby the polymer subunits capable of forming the hydrogel polymer constituent polymerise to form the hydrogel polymer constituent and subsequently form the hydrogel and, at the same time, the polymer subunits capable of forming the conductive polymer polymerise to form the conductive polymer within the hydrogel.

In a third aspect, the present invention provides a method for producing a polymeric material in which a conductive polymer is substantially homogeneously distributed within a hydrogel. The method comprises:

forming a hydrogel from one or more hydrogel polymer constituents;

exposing the hydrogel to polymer subunits capable of forming the conductive polymer; and polymerising the polymer subunits, whereby the conductive polymer is formed within the hydrogel.

In some embodiments of the method of the third aspect, the hydrogel is exposed to the polymer subunits capable of forming the conductive polymer by forming the hydrogel in a solution comprising the polymer subunits. In alternate embodiments, the hydrogel is exposed to the polymer subunits capable of forming the conductive polymer by contacting the hydrogel with a solution comprising the polymer subunits.

In some embodiments of the method of the second and third aspects, at least one of the hydrogel polymer constituents comprises covalently bound anionic species, where the anionic species are dopants around which the conductive polymer is formed.

In some embodiments of the method of the second and third aspects, the hydrogel is formed on a conductive substrate and the polymer subunits capable of forming the conductive polymer are polymerised by applying an electrical current through the hydrogel. Typically, the polymer subunits capable of forming the conductive polymer are caused to slowly polymerise.

In alternative embodiments of the method of the second and third aspects, the conductive polymer is chemically synthesised (e.g. by oxidative coupling).

In some embodiments of the method of the second and third aspects, the hydrogel is exposed to a biologically active substance, which is incorporated into the polymeric material.

In some embodiments of the method of the second and third aspects, the polymeric material is the polymeric material of the first aspect.

In a fourth aspect, the present invention provides a method for producing a conductive polymer surface on a substrate. The method comprises:
 coating the substrate with a first conductive polymer;
 forming a hydrogel on the coated substrate from one or more hydrogel polymer constituents;
 diffusing polymer subunits capable of forming a second conductive polymer throughout the hydrogel; and
 polymerising the polymer subunits, whereby the second conductive polymer is formed within the hydrogel and is substantially homogeneously distributed within the hydrogel.

Embodiments of the method of the fourth aspect may be similar to those described herein with reference to the second and third aspects.

In a fifth aspect, the present invention provides a device comprising a conductive surface, wherein the polymeric material of the first aspect is deposited on the conducting surface.

In a sixth aspect, the present invention provides an electrode comprising at least one surface onto which the polymeric material of the first aspect has been deposited.

In a seventh aspect, the present invention provides a substrate coated with a polymeric material comprising a conductive polymer substantially homogeneously distributed within a hydrogel.

In an eighth aspect, the present invention provides the use of the polymeric material of the first aspect in a device (e.g. a bioelectrode) that is implantable into a patient.

In a ninth aspect, the present invention provides the use of a hydrogel to increase the durability of a conductive polymer.

DETAILED DESCRIPTION OF THE INVENTION

As discussed above, the present invention provides a polymeric material comprising a conductive polymer substantially homogeneously distributed within a hydrogel.

A conductive polymer is any polymer that is capable of conducting electricity. Conductive polymers are unsaturated polymers containing delocalised electrons and an electrical charge. Incorporating the conductive polymer into the polymeric material of the present invention results in a polymeric material that is conductive, but which has superior physical and chemical properties over the conductive polymer itself.

Suitable conductive polymers for use in the present invention include polypyrrole and its derivatives, polythiophene and its derivatives, phenyl mercaptan and its derivatives, polyaniline and its derivatives, polyindole and its derivatives, polycarbazole and its derivatives, as well as copolymers and/or combinations thereof. Suitable derivatives are those that contain functional groups, such as a methoxy group. Examples within the range of other optional functional groups are alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulfonyloxy, arylsulfenyloxy, heterocyclyl, heterocycloxy, heterocyclamino, haloheterocyclyl, alkylsulfenyl, arylsulfenyl, carboalkoxy, carboaryloxy, mercapto, alkylthio, benzylthio, acylthio, sulfonate, carboxylate, phosphonate and nitrate groups or combinations thereof. The hydrocarbon groups referred to in the above list are preferably 10 carbon atoms or less in length, and can be straight chained, branched or cyclic.

Suitable conductive polymers for use in the present invention include poly(3,4-ethylene dioxythiopene), poly(hydroxymethyl-3,4-ethylenedioxythiopene), poly(3-alkylthiophene), polypyrrole, polyaniline (emeraldine base) or combinations thereof.

A hydrogel is a network of hydrophilic polymer constituents where water fills the space between macromolecules and the density of the hydrogel is not significantly different to that of water. Typically, the polymer constituents are cross-linked via chemical or physical processes such that they form a "mesh-like" insoluble polymer network. However, such extensive cross-linking may not be necessary, for example, in the case of hydrogels in the form of polymer brushes. The mechanical properties of a hydrogel can be controlled by modifying the amounts and types of polymer constituent, as well as the cross-link density between the hydrophilic polymer constituents.

Any hydrogel may be used in the polymeric material of the present invention, provided that the conductive polymer is substantially distributed throughout the hydrogel in the resultant polymeric material. Typically, the hydrogel comprises a polymer constituent having covalently bound anionic species, the anionic species being dopants for the conductive polymer. As noted above, a conductive polymer requires a dopant (e.g. an ionically charged species) in order for the polymer to form and be capable of passing electronic or ionic charges. Such dopants are typically sulfonated molecules (e.g. p-toluene sulfonic acid (pTS)), but the inventors have discovered that providing dopants in the form of anionic species covalently bound to the polymer constituent of the hydrogel causes the conductive polymer to be formed intimately with the polymer constituents of the hydrogel, which results in an integrated polymeric material instead of the phase separated polymeric material produced by existing processes.

The polymer constituent having covalently bound anionic species may be a polymer that inherently contains an anionic charge in its backbone, or may be a polymer that has been modified to include a covalently bound anionic species. For example, polymer constituents such as DNA, heparin, alginate and chondroitin sulphate contain anionic species in their polymer backbones. Synthetic polymers or biopolymers such as peptides, proteins or saccharides having a specific bioactivity can be anionically modified using methods known in the art. For example, biopolymers can be functionalised by chemically modifying their end groups to create an overall anionic charge. For example laminin peptides can be modified by the addition of specific amino acids which create an anionic tail or side chain that would allow it to dope a conducting polymer whilst retaining its bioactivity.

It is also possible to dope a conductive polymer with a cationic species. However, many cationically doped conductive polymers are unstable or not environmentally friendly.

The hydrogel may comprise two or more polymer constituents in order to take advantage of the properties each of those polymer constituents impart on the resultant hydrogel. For example, certain polymer constituents are known to provide specific material structure, physical and chemical properties (e.g. surface texture, hardness, mechanical strength and elasticity, water content, tissue compatibility, etc) to a hydrogel formed from those polymer constituents. Thus, a hydrogel having desired physical and chemical properties (e.g. long term mechanical and chemical stability) can be provided by adjusting the type and proportion of polymer constituents in a hydrogel.

The hydrogel may include at least one polymer constituent that is a biopolymer (i.e. a polymer produced by a living organism or a synthetically produced mimic of a biologically sourced molecule, which has similar bioactivity when placed in a biological environment), especially if the polymeric material is intended for use in medical science applications (e.g. on medical electrodes). Suitable biopolymers include heparin, hyaluronan, chondroitin sulphate, keratan sulphate, alginate, chitosan, fibrin, oligonucleotides, DNA, RNA, silk like polymer with fibronectin fragments (SLPF), gylcoproteins including collagen, laminin, fibronectin, vitronectin and fibrinogen, as well as their peptides, poly(amino acids), silk proteins, synthetic peptide sequences and combinations thereof.

Other functional biological molecules could be used as the polymer constituents of the hydrogel (or polymerized to form the polymer constituents of the hydrogel) in order to take advantage of desirable properties of the biological molecules. For example, a heparin hydrogel could be used for some neural applications, and other biofunctional proteins and peptides including laminin peptides, poly(amino acids) and silk proteins such as sericin (which have specific neural cell interfacing properties) could also be included in the polymeric material for specific medical applications.

Oligonucleotides, such as small interfering ribonucleic acids (siRNA) could also be used to form the hydrogel. As oligonucleotides have a net negative charge, they are ideal for doping conductive polymers.

The hydrogel may include at least one polymer constituent that is a synthetic polymer (i.e. a polymer that is not produced by a living organism). Suitable synthetic polymers include polyvinyl alcohol, polyethylene glycol, poly(acrylic acid) and its derivatives; poly(ethylene oxide) and its copolymers, polyphosphazene, silicones, polyacrylamides, polyvinylpyrrolidones, poly-hydroxyethylmethacrylate, poly(styrene sulfonate) and combinations thereof. Specific synthetic polymers can be chosen based on the properties they will impart on the resultant hydrogel.

If a selected polymer constituent (either synthetic or biological) of the hydrogel does not include groups capable of cross-linking the polymer constituent with other polymer constituent(s) to thereby form the hydrogel, then the polymer constituent is first modified to include such groups. For example, acrylate crosslinkers could be used to functionalise polymer constituents (e.g. heparin) using established methods, if necessary. The acrylate modified polymer constituents are subsequently caused to react, whereby they cross-link with other polymer constituents to form the hydrogel.

In a specific embodiment, the hydrogel comprises heparin and polyvinyl alcohol (PVA). Heparin is a biopolymer that has a high negative charge density in its polymer backbone, which enables it to dope the conductive polymer. PVA is a synthetic polymer often used in hydrogels because it imparts good elasticity and other physical properties to the resultant hydrogel. The inventors have shown that heparin can be modified with methacrylates and thereby cross-linked into conventional synthetic hydrogels such as PVA to produce bioactive hydrogels. The inventors believe that the bioactivity of heparin is preserved within the hybrid hydrogel, which would make such a hybrid hydrogel useful in neural applications because it would be expected to be more biocompatible.

The conductive polymer and hydrogel are substantially homogenously distributed within the polymeric material. That is, the polymeric material contains the conductive polymer and hydrogel polymer constituents in an intimate mixture, and the polymers are not phase separated to any substantial degree.

The ratio of conductive polymer to the hydrogel in the polymeric material will affect the properties of the polymeric material. Any ratio of conductive polymer to hydrogel may be used, provided that a useful product is formed. If the ratio of conductive polymer to hydrogel is too low, then the resultant polymeric material would not conduct electricity. If the ratio of conductive polymer to hydrogel is too high, then the resultant polymeric material would be less likely to have the desirable physical properties of the hydrogel.

Typically, the ratio of conductive polymer to hydrogel will vary from about 0.2:1 to about 1:0.2 (e.g. from about 0.5:1 to 1:0.5, from about 0.8:1 to 1:0.8 or about 1:1).

Polymeric materials of the invention typically include from about 10% to about 30% (by weight) of the polymer constituent of the hydrogel in order for the hydrogel to have a sufficient mass transport capability to allow the monomers of the conductive polymer to readily diffuse during polymerization. The conductive polymer portion of the hybrid can be formed using concentrations of monomer of from about 0.01 M to about 0.2 M (e.g. from about 0.01 M to about 0.1 M or from about 0.05 M to about 0.1 M).

As noted above, hydrogels contain a high proportion of water and are well suited to incorporating additional substances (especially water soluble substances) into the hydrogel matrix. Thus, if, for example, the polymeric material of the invention is intended for use in medical science applications (e.g. as a medical electrode), a biologically active substance may be incorporated into and distributed within the hydrogel (in addition to any biopolymer that forms part of the hydrogel). Examples of suitable biologically active substances include neurotrophins and other growth factors, anti-inflammatory drugs (e.g. to reduce local swelling after insertion of the polymeric material), antibiotics, siRNA and combinations thereof.

The inventors believe that the polymeric materials of the present invention can deliver much higher concentrations of biologically active substances (e.g. neurotrophins, anti-inflammatory drugs and siRNA) than could conventional conductive polymers, because of the drug delivery functionality of the hydrogel component. The polymeric materials of the present invention can therefore be tailored for specific cell interactions, including rescue of damaged and diseased tissues, as well as for possible gene therapy applications. To perform these functions, various biological molecules can be loaded within the hydrogel matrix of the polymeric material at concentrations high enough to stimulate a cellular response. The biological molecules could be delivered from the polymeric materials via passive diffusion and/or electrically stimulated delivery. The polymeric materials of the present invention could also be used to deliver multiple biologically active substances, such as combinations of neurotrophins and anti-inflammatory drugs for a consolidated approach to neural engineering.

One type of biological molecule that can be incorporated into the hydrogel is the growth factor family. Supply of appropriate types and concentrations of growth factors can significantly improve repair and rescue of neural tissue. Integration of growth factors within the polymeric materials of the present invention could be achieved during polymerisation (in which the growth factor is added to the hydrogel polymer constituent solution), or they could be loaded post-fabrication using hydrogel swelling as a driving force for uptake.

As discussed above, the polymeric materials of the present invention combine the desirable properties of a conductive polymer (i.e. electroactivity) with the desirable properties of a hydrogel (e.g. durability and elasticity etc).

The polymeric material of the present invention has an elasticity and mechanical modulus that is better than that of the conductive polymer itself (i.e. the polymeric material of the present invention has a higher elasticity and lower hardness than the conductive polymer). The elasticity of the polymeric material can be quantified by the Young's modulus using standard techniques in the art. In some embodiments, the polymeric material has a Young's modulus of from about 1 kPa to about 10 MPa (e.g. from about 10 kPa to about 25 kPa, from about 100 kPa to about 500 kPa or from about 10 kPa to about 5 MPa). The most elastic conductive polymer known (the chemically synthesised PEDOT:PSS) has a Young's modulus of approximately 1 GPa, which is much higher than PVA, which has a Young's modulus of 20-1500 kPA. The inventors have found that the polymeric material of the present invention can reduce the stiffness of a CP by up to five orders of magnitude, bringing it within one order of magnitude of neural tissue stiffness (which has a Young's modulus of 0.1-1.5 kPa).

The hydrated force moduli of an exemplary hydrated polymeric material of the present invention containing poly(3,4-ethylene dioxythiophene), poly(vinyl alcohol) and heparin-methacrylate (PEDOT/PVA-HepMA), as well as those of its component hydrogel (PVA-HepMA) and conductive polymer (PEDOT) was measured using techniques known in the art. The exemplary polymeric material of the present invention was found to have a compression modulus of about 3 kPa, which is comparable to that of neural tissue. In contrast, the compression moduli of the hydrogel and conductive polymer under identical conditions were 0.3 kPa and 100 kPa respectively.

Additional material properties of the polymeric materials of the present invention which can be assessed include physical properties such as surface topography and adhesion to a substrate, as well as its electrical and chemical properties. Such properties can be analysed visually using scanning electron microscopy (SEM), mechanically using nanoindentation and electrically through impedance spectroscopy (EIS) and cyclic voltammetry (CV).

The chemical structure and degree of integration between components of the polymeric materials of the present invention can be determined using solid-state nuclear magnetic resonance (NMR) and cryogenic transmission electron microscopy (cryo-TEM). The detailed microstructure can be studied as a function of conversion by cryo-TEM.

A number of methods may be used to manufacture the polymeric material of the present invention. As will be appreciated, the mechanisms by which the hydrogel-conducting polymer networks are formed may affect the resulting properties of the polymeric material. Ideally, such methods will be adapted to produce polymeric materials of the present invention which have long-term mechanical and electrical stability.

In one method, the polymeric material of the invention is produced by:
  mixing polymer subunits capable of forming a hydrogel polymer constituent with polymer subunits capable of forming the conductive polymer, and then
  exposing the mixture to conditions whereby the polymer subunits capable of forming the hydrogel polymer constituent polymerise to form the hydrogel polymer constituent which subsequently cross-link with each other to form the hydrogel and, at the same time, the polymer subunits capable of forming the conductive polymer polymerise to form the conductive polymer within the hydrogel.

In one method, the polymeric material of the invention is produced by:
  forming a hydrogel from one or more hydrogel polymer constituents;
  exposing the hydrogel to polymer subunits capable of forming the conductive polymer; and
  polymerising the polymer subunits, whereby the conductive polymer is formed within the hydrogel.

The hydrogel may be exposed to the polymer subunits capable of forming the conductive polymer by forming the hydrogel in a solution comprising the polymer subunits. Alternatively, the hydrogel may be exposed to the polymer subunits by contacting the formed hydrogel with a solution comprising the polymer subunits.

In one method, a conductive polymer surface on a substrate is produced by:
  coating the substrate with a first conductive polymer;
  forming a hydrogel on the coated substrate from one or more hydrogel polymer constituents;
  diffusing polymer subunits capable of forming a second conductive polymer throughout the hydrogel; and
  polymerising the polymer subunits, whereby the second conductive polymer is formed within the hydrogel and is substantially homogeneously distributed within the hydrogel.

The term "polymer subunit" is used herein to refer to monomers, dimers, multimers (e.g. oligomers) and mixtures thereof that, upon polymerisation, form a polymer (either a hydrogel polymer constituent or a conductive polymer). The polymer subunits which form the polymer may be the same or different. Furthermore, the dimer and multimer may be formed from monomer units which are the same or different. Consequently, the polymer may be a homopolymer or a copolymer.

The polymer subunits may be polymerised by any process appropriate for the particular monomers involved. This encompasses addition polymerisation or condensation polymerisation, with free radical initiation, where required, produced by redox reaction, light or microwave. Usually the polymerisation is by way of addition polymerisation for the production of the polymer.

In some embodiments, the hydrogel is formed on a conductive substrate and the polymer subunits capable of forming the conductive polymer are polymerised by applying an electrical current through the hydrogel. Typically, the conductive polymer is electrodeposited onto the conductive substrate.

The inventors have found that slowly polymerising the conductive polymer within the hydrogel can result in a more intimate mixture of the conductive polymer and hydrogel. Thus, polymerisation of the polymer subunits capable of forming the conductive polymer is typically caused to occur slowly. For example, in embodiments where the conductive polymer is formed electrochemically, the conductive polymer may be caused to polymerise by applying an electrical current of between about 0.1 to 1 $mA/cm^2$ for between about 30 mins to 1 hour. This slow polymerisation (compared to conventional depositions performed at 1 $mA/cm^2$-4 $mA\,cm^2$ for 1-15 min) results in a more uniform distribution of the conductive polymer through the hydrogel.

In some embodiments, however, especially when the conductive polymer is particularly bulky, the conductive polymer may be caused to polymerise by applying an electrical current of up to about 4 $mA/cm^2$. Furthermore, in some embodiments, polymerisation may be caused to occur more quickly, for example by applying a relatively high current for as little as 1 min. Whilst such polymeric materials may have a less organised structure, this may be acceptable in some applications.

Alternatively, the conductive polymer may be chemically synthesised using methods known in the art, such as oxidative coupling.

In embodiments in which the polymeric material of the invention is to be provided on a conductive surface (e.g. metal electrode), a pre-coating of a conductive polymer may be electrodeposited on the conductive substrate before the hydrogel is formed. The inventors have found that such pre-coating can greatly improve the bond between the substrate and the hydrogel, resulting in a more durable product. Indeed, the inventors believe that coating a substrate with a conductive polymer before any type of polymeric material is bound to the substrate may result in a more secure attachment of the polymer to the substrate.

Four specific methods for preparing the polymeric material of the invention are described below. These methods are (1) electrodeposition of a conductive polymer through an ionic hydrogel; (2) chemical synthesis of the conductive polymer entrapped within a hydrogel; (3) polymerisation of a conductive polymer throughout pre-fabricated nanoscale polymer brushes; and (4) deposition and polymerisation of a conductive polymer in hydrogel microspheres.

Method 1—Electrodeposition of a Conductive Polymer Through an Anionically Charged Hydrogel This method utilises conventional techniques for the electrodeposition of conductive polymers. However, doping of the conductive polymer is mediated by anions in the cross-linked hydrogel (as opposed to conventional doping using free ions such as pTS). In a first step, the polymer constituents of the hydrogel are linked to a conductive substrate and, in the second step, the conductive polymer is electrodeposited by application of a constant current or constant voltage through an electrolyte overlying the hydrogel which contains the polymer subunits (e.g. monomers) capable of forming the conductive polymer. The polymer constituents of the hydrogel have covalently linked dopants (in the form of anionic species), which causes the conductive polymer to polymerise intimately with the hydrogel polymers within the hydrogel mesh.

Such methods may utilize a biosynthetic hydrogel such as PVA blended with anionic heparin-methacrylate or a pure biological hydrogel such as alginate, and a thermal and electrochemically stable thiophene such as the poly(ethylene dioxythiophene) (PEDOT) derivative as the conductive polymer.

Method 2—Chemical Polymerisation of a Conductive Polymer within a Hydrogel from Mixed Precursors This method involves the fabrication of the polymeric material from mixed precursors. The polymer constituents of the hydrogel are exposed to polymer subunits capable of forming the conductive polymer (e.g. by mixing solutions of the hydrogel polymer constituents and the polymer subunits) such that the polymer subunits capable of forming the conductive polymer become entrapped within the hydrogel polymer constituents. Following cross-linking of the hydrogel polymer constituents to form the hydrogel, the product is dried and rehydrated in a strong oxidant, which polymerises the polymer subunits to form the conductive polymer.

This method allows for more controlled conductive polymer structures to be formed, with regioregular orientation of the polymer subunits. Since chemically synthesised conductive polymers may have less inherent electroactivity, voltage cycling may improve orientation of the polymer to allow better alignment with the anionic hydrogel matrix.

Method 3—Polymerisation of Conductive Polymer Through Nanoscale Polymer Brushes

In this method, surface grafted polymer brushes are used to create a controlled and uniform polymeric material. Polymer brushes are produced on electrically conductive substrates (e.g. metals, indium tin oxide, semiconductors or conducting polymers) using surface initiated living radical polymerisation (SI-LRP) techniques (e.g. atom transfer radical polymerisation (ATRP), nitroxide mediated polymerisation (NMP) or reversible addition fragmentation chain transfer polymerisation (RAFT)). The chain length and spacing of these brushes can be varied in order to change the properties of the resulting polymeric material.

Once grafted, the hydrophilic polymer chains are modified if necessary to include cross-linking groups and/or anionic species (for example, by attaching anionic peptides or heparin-MA).

The resultant surface grafted polymer brushes are then caused to cross-link with each other to form a hydrogel and then exposed to polymer subunits capable of forming the conductive polymer. Alternatively, the polymer brushes may be exposed to the polymer subunits capable of forming the conductive polymer before they are cross-linked. Alternatively, the polymer brushes may not need to be cross-linked with each other because they are already configured to entrap water and hence be a hydrogel. The interactions between the hydrogel brush and the polymer subunits from which the conductive polymer is evolved will affect the resulting hybrid structure and properties of the polymeric material. Either electrodeposition or chemical synthesis methods (or a combination of both methods) could then be used to produce an integrated network of conductive polymers throughout the brush structure.

Method 4—Deposition and Polymerisation of a Conductive Polymer in Hydrogel Microspheres In this method, hydrogel precursors (synthetic and/or biopolymers) are formed into microspheres by either electrospraying or emulsification and subsequently cross-linked in solution. The microspheres are then filtered out and the conductive polymer precursors are added to the microspheres. The conductive polymer is then polymerised (either using chemical polymerisation techniques or by causing the microsphere to settle onto an electrode and then using electropolymerising techniques) within the microspheres to form the polymeric material of the present invention.

Providing the polymeric material of the present invention in the form of such microspheres would enable multiple types of biological molecules to be incorporated into a synthetic support with the aim of providing the appropriate milieu for cell rescue and function. Microspheres containing different components and hence having different biological functions can be added to the same bulk material and supplied at known and complimentary concentrations. Additionally, the microsphere structure allows dimensional control of the material on both a micron and nanometer scale, which enables surface properties to be designed for specific cell interactions.

The polymeric materials of the present invention will be useful in any technology that requires a conductive, durable and elastic polymeric material. It is envisaged that the polymeric materials of the present invention could be used in a wide range of industries spanning from microelectronics to medical science.

The present invention therefore also relates to a device comprising a conductive surface, wherein the polymeric material of the invention is deposited on the conducting surface.

The present invention therefore also relates to an electrode comprising at least one surface onto which the polymeric material of the invention has been deposited.

The present invention therefore also relates to a substrate coated with a polymeric material comprising a conductive polymer substantially homogeneously distributed within a hydrogel.

The present invention therefore also relates to the use of the polymeric material of the invention in a device (e.g. a bioelectrode) that is implantable into a patient.

With the advent of more sophisticated electronic devices and the capability to manufacture smaller electrodes, conductive polymers have enormous potential for a wide range of uses. For example, conductive polymers hold significant promise as electrode coatings because they decrease impedance and improve biological performance. However, their inherently poor long-term mechanical and electrical performance properties can be exacerbated by the incorporation of integral biological molecules. Furthermore, in the biomedical field, the additional limiting factors to implementation of low impedance conductive polymers in electrode applications relate to facilitating biological recognition and producing stable integration of excitable tissue with the electrode coating material.

The polymeric material of the present invention is conductive and, due to the hydrogel component, capable of improving the biocompatibility and mechanical performance of electrodes. Furthermore, the high hydrophilicity of the hydrogel provides a substantial reservoir for the incorporation of biological molecules such as neurotrophins and anti-inflammatories.

Accordingly, one significant application of the polymeric materials of the present invention is in the field of medical electrodes. Conductive polymers have been investigated as electrode coatings which can provide biological signals to the surrounding tissues through the use of biofunctional dopant ions and/or entrapped biomolecules which are released following implantation. However, the capacity of such bioactive conductive polymers to provide stable, robust connections between the nerve cells and implant electrodes remains an unmet challenge due to the limited concentrations of biomolecules which can be incorporated within a conductive polymer matrix. The polymer material of the present invention addresses this limitation because it can carry functional biological molecules within the structural biosynthetic hydrogel backbone, as well act as a reservoir for water soluble biological signalling factors.

The polymeric material of the present invention may also find application in electronically conducting adhesives and antistatic coatings for the microelectronics industry, polymer lithium ion batteries, polymer light emitting diodes (LEDs), solar cells, biosensors, artificial muscles, tactile sensors and neuroprosthetic electrodes.

EXAMPLES

Example 1

An example in which a hybrid conductive polymer-hydrogel polymeric material is formed on the surface of a platinum electrode will now be described.

Two poly(ethylene dioxythiopene) (PEDOT) solutions were prepared including the components listed in Table 1. EDOT is an abbreviation for 3,4-ethylenedioxylthiophene, the monomer from which PEDOT is formed.

Two hydrogel solutions were prepared including the components listed in Table 2 using standard techniques.

TABLE 1

Conductive polymer solutions (per mL)

| Constituents | PEDOT/pTS (pre-layer) | PEDOT (no dopant) |
| --- | --- | --- |
| $H_2O$ | 0.5 mL | 1 mL |
| Acetonitrile | 0.5 mL | — |
| EDOT | 0.1M or 10.7 µL | 0.03M or 3.2 µL |
| pTS | 0.05M or 10.3 mg | |

TABLE 2

Hydrogel solutions

| Constituents | PVA-HepMA (amounts for 1 mL) | PVA-HepMA-NGF (amounts for 0.25 mL only) |
| --- | --- | --- |
| PVA | 18% or 0.18 g | 18% or 45 mg |
| Hep-MA (anionic hydrogel) | 2% or 0.02 g | 2% or 5 mg |
| $H_2O$ | 0.7 g | 175 mg |
| Initiator | 1% or 0.1 g | 1% or 25 mg |
| NGF | — | 4 µg/mL or 100 mg |

A pre-layer of PEDOT/pTS was first deposited onto the laser treated surface of two Pt electrodes to assist in binding the conductive polymer-hydrogel polymeric materials to the electrode. In this step, the PEDOT/pTS solution was placed over the Pt electrode to form a tensioned droplet with the circular Pt counter electrode. The working electrode was formed by placing a conductive substrate beneath the sample electrode and connected using an alligator clip. The pre-layer of PEDOT/pTS was then deposited at 1 mA/cm$^2$ using galvanostatic (constant current) polymerisation for 1 min.

The pre-coated surfaces were then washed with excess DI water and dried for 30 min. 10 µL of each of the hydrogel solutions was then placed onto each electrode and covered with a cover slip. The solutions were then exposed to UV light for 180 s and the cover slip was removed. The hydrogel coated electrodes were soaked in DI water for 12 hours to remove unreacted reagents and mobile dopant units.

The PEDOT (no dopant) solution was then deposited over the hydrogels and caused to polymerise within the hydrogel matrix and be galvanostatically deposited on the coated Pt electrode by applying 0.5 mA/cm$^2$ for 30 min (in 5 min increments, using a refreshed electrolyte solution each time). All samples were then washed with DI water three times and then placed in TCP wells with 0.5 mL DI or Baxter water.

Mechanically, the samples prepared as described above have a significantly reduced stiffness (by two orders of magnitude) compared to conventional samples containing only PEDOT, as measured by hydrated peak force compression moduli. The reduction in interface stiffness is expected to improve interactions at the implant interface by reducing damage to neural tissue. Further, the hydrogel component of the samples imparts the required mechanical softness and elasticity required to dampen the effects of the metallic electrodes.

The hybrid samples (both with and without NGF) had similar electroactivity to homogeneous PEDOT/pTS controls, but had greater stability when subjected to repeat cyclic voltammetry. The NGF loaded sample was found to be able to stimulate neurite outgrowth in cloned neural cells.

Example 2

Two different hydrogels were used in this Example; the first formed from 18% (w/v) poly(vinyl alcohol) (PVA) crosslinked with 2% (w/v) heparin-methacrylate (HepMA), and the second being a 30% (w/v) HepMA homogenous hydrogel. The HepMA in the hydrogel structure provides covalently bound anionic dopants, which mediate the formation of conduction bands during electropolymerisation of the conductive polymer, poly(ethylene dioxythiophene) (PEDOT), through the hydrogel mesh.

Methods similar to those described in Example 1 were used to prepare the PEDOT-hydrogel hybrid polymeric materials. X-ray photoelectron spectroscopy (XPS) and cross-sectional scanning electron microscopy (SEM) with EDS capability was used to confirm that the conductive polymer was substantially homogenously distributed throughout the hydrogel.

The surface morphology of the samples was examined using SEM. Hybrid materials have a distinctive surface morphology in comparison to conventional conductive polymers. Whilst homogenous conductive polymers have a highly nodular morphology across the entire film, the hybrid has a visible hydrogel surface with an underlying more uniform and controlled nodularity, consistent with the formation of a conductive polymer. The PEDOT formed throughout the hydrogel, with nodules apparent both at the surface and beneath the visible planar hydrogel surface.

The thickness of these films have been measured between 2 μm and 20 μm by cross-sectional SEM. When the pre-layer is not employed the polymeric material can be floated off the underlying conductive substrate to form a standalone material.

Charge storage capacity (CSC), measured by cyclic voltammetry, confirmed that the crosslinking of anionic HepMA with PVA in the hydrogel successfully introduces doping ions to the hydrogel. The covalently bound 2% HepMA within the PVA co-polymer hydrogel does not dope the PEDOT as fully as the conventional sulfonate ion, pTS. The 30% HepMA hydrogels were created in an attempt to impart better doping and a greater charge carrying capacity to the hybrid system. The CSC determined from CV indicated that the highly anionic homogenous heparin hydrogel provided better doping during PEDOT polymerisation, increasing the final CSC by 37% from 45 mC/cm$^2$ up to 71.5 mC/cm$^2$, compared to the PVA-HepMA hydrogel.

Continual cycling demonstrated that both of the hybrid CP-hydrogels were able to maintain their electroactivity across an extended period of redox cycling, with improved stability compared to PEDOT/pTS controls (i.e. polymeric materials containing only a conductive polymer). The PEDOT/pTS control underwent a loss of 49% of its original electroactivity (established from the CSC at Cycle 1) over 850 cycles, compared to a loss of only 28% for both hybrid variants. Without wishing to be bound by theory, the inventors believe that this is due to the HepMA ions being covalently bound within the hybrid system, which prevents them from diffusing away from the electrode interface during cycling.

Biphasic stimulation voltage waveforms recorded from electrode materials provide conventional metrics for neuroprosthetic applications. The end of phase 1 voltage is commonly used to establish the charge injection limit of a material. Using this technique, it has been found that typical stimulations (phase length of 0.2 ms with stimulation amplitude of 0.25 mA) produce an end of phase 1 voltage of 0.1V for the hybrid polymeric materials described earlier in this Example, which is an order of magnitude lower than for platinum electrodes, which have an end of phase 1 voltage of 2.5V. This voltage is comparable to homogenous conducting polymers, which have a voltage of 0.15V under the same stimulation conditions. When the charge was increased to find the limit at which the electrodes will function in the application (i.e. in a stimulating medical electrode or neuroprosthetic device), it was found that the hybrid limit was 1.25 mC/cm$^2$, compared to bare platinum with a limit of 0.2 mC/cm$^2$.

As a potential material for neural prosthetic and other implant applications, the hybrid system must also have suitable interactions with neural tissue. In vitro studies using the model neural clone PC12 demonstrated that both of the hybrid CP-hydrogels discussed above are compatible with biological tissues. Although adherence to the substrate was reduced compared to a standard conductive polymer control, the neurite outgrowth was significantly improved compared to bare Pt (the reduced cell adherence is probably due to the lower surface roughness of the hybrid).

Example 3

An example of methods used to prepare conductive polymer-hydrophilic polymer brushes are described below.

Poly(2-hydroxyethyl methacrylate) (PHEMA) polymer brushes were grafted on a gold coated silicon substrate via atom transfer radical polymerisation (ATRP). In this ARTP process, thiol surface initiators were immobilized on the gold substrate, and PHEMA was grafted onto the substrate to form a polymer brush by ATRP reaction using 1.1M CuBr/2.2M 2,2'-bipyridine/350M HEMA/1M ethyl bromoisobutyrate in methanol. The length of the dry brushes measured by ellipsometry was 24.7 nm and their molecular weight (Mn) was 38600 with PDI 1.15.

The brushes were soaked in an aqueous solution of 0.01M EDOT for 30 mins and an electrical charge of 0.5 C/cm$^2$ was then applied through the solution to deposit a thin transparent blue layer of conductive polymer through the brushes. XPS confirmed the presence of both the hydrogel and conductive polymers at the hybrid surface.

Similar techniques can be used to prepare anionic polystyrene sulfonate polymer brushes by grafting the polymers onto a gold substrate using ARTP with 0.7M Cu(I)Br/0.3M Cu(II)Br/2M 2,2'-bipyridine/200M sodium styrene sulfonate/1M ethyl bromoisobutyrate in methanol.

It will be understood to persons skilled in the art of the invention that many modifications may be made without departing from the spirit and scope of the invention. For example, it is envisaged that the present invention may also provide for the use of a hydrogel to increase the durability of a conductive polymer.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A polymeric material comprising an electrodeposited conductive polymer substantially homogeneously distributed within a hydrogel, wherein the hydrogel comprises a cross-linkable biopolymer that exhibits bioactivity, in which the biopolymer is covalently cross-linked with a synthetic polymer, the biopolymer further having covalently bound anionic species which provide doping for the electrodeposited conductive polymer.

2. The polymeric material of claim 1, wherein the covalently bound anionic species are in the backbone of the biopolymer.

3. The polymeric material of claim 1, wherein the biopolymer is a polymer produced by a living organism and modified to include the covalently bound anionic species.

4. The polymeric material of claim 3, wherein the covalently bound anionic species is an anionic side chain grafted onto the biopolymer.

5. The polymeric material of claim 1, wherein the biopolymer is selected from heparin, hyaluronan, chondroitin sulphate, keratin sulphate, alginate, chitosan, fibrin, oligonucleotides, DNA, RNA, silk like polymer with fibronectin fragments (SLPF), glycoproteins including collagen, laminin, fibronectin, vitronectin and fibrinogen and their peptides, poly(amino acids), silk proteins or combinations thereof.

6. The polymeric material of claim 1, wherein the hydrogel comprises at least one polymer constituent that is a synthetic polymer.

7. The polymeric material of claim 6, wherein the synthetic polymer is selected from polyvinyl alcohol, polyethylene glycol, poly(acrylic acid) and its derivatives; poly(ethylene oxide) and its copolymers, polyphosphazene, silicones, polyacrylamides, polyvinylpyrrolidones, poly-hydroxy ethylmethacrylate, poly(styrene sulfonate) or combinations thereof.

8. The polymeric material of claim 1, wherein the hydrogel comprises functionalized heparin covalently cross-linked with polyvinyl alcohol.

9. The polymeric material of claim 1, wherein the conductive polymer is selected from polypyrrole and its derivatives, polythiophene and its derivatives, phenyl mercaptan and its derivatives, polyaniline and its derivatives, polyindole and its derivatives, polycarbazole and its derivatives, or copolymers or combinations thereof.

10. The polymeric material of claim 1, wherein the conductive polymer is selected from poly(3,4-ethylene dioxythiopene), poly(hydroxymethyl-3,4-ethylenedioxythiopene), poly(3-alklythiophene), polypyrrole, polyaniline (emeraldine base) or combinations thereof.

11. The polymeric material of claim 1, wherein the polymeric material further comprises a biologically active substance distributed within the hydrogel.

12. The polymeric material of claim 11, wherein the biologically active substance is selected from neurotrophins, anti-inflammatory drugs, antibiotics, siRNA or combinations thereof.

13. The polymeric material of claim 1, wherein the conductive polymer and the hydrogel are present in the polymeric material in a ratio of from about 0.2:1 to about 1:0.2.

14. The polymeric material of claim 1, wherein the hydrogel constitutes from about 10% to about 30% by weight of the polymeric material.

15. The polymeric material of claim 1, wherein the polymeric material has a Young's modulus of from about 1 kPa to about 10 MPa.

* * * * *